United States Patent [19]

Sekula et al.

[11] Patent Number: 5,571,935
[45] Date of Patent: Nov. 5, 1996

[54] PROCESS FOR PRODUCING ESTERIFIED ALKOXYLATED POLYOLS WITH IMPROVED STABILITY

[75] Inventors: Bernard C. Sekula, High Bridge; Thaddeus R. Ziegert, Hackettstown, both of N.J.; Michael R. Ferenz, Coatesville, Pa.

[73] Assignee: CPC International Inc., Englewood Cliffs, N.J.

[21] Appl. No.: 182,267

[22] Filed: Jan. 14, 1994

[51] Int. Cl.$^6$ .................................................. C11C 3/00
[52] U.S. Cl. .......................... 554/168; 554/2; 554/149; 554/167; 554/227; 252/407
[58] Field of Search ..................... 554/149, 227, 554/2, 168, 167; 252/407

[56] References Cited

U.S. PATENT DOCUMENTS 4,983,329  1/1991  Cooper ................................. 260/410
5,155,244  10/1992  Greene et al. ......................... 554/2

FOREIGN PATENT DOCUMENTS 0376090  7/1990  European Pat. Off. .

OTHER PUBLICATIONS

European Search Report EP 95 10 0200.

*Primary Examiner*—Gary Geist
*Assistant Examiner*—Deborah D. Carr

[57] ABSTRACT

Esterified alkoxylated polyols, particularly a fatty acid-esterified propoxylated glycerol, which exhibit improved flavor and oxidative stability by the addition of antioxidants to the alkoxylated polyols, either prior to or subsequent to steam stripping, fatty acids or combinations thereof prior to fatty acid esterification, and the products thereof.

21 Claims, 3 Drawing Sheets

PROCESS FOR PRODUCING ESTERIFIED ALKOXYLATED POLYOLS WITH IMPROVED STABILITY

FIELD OF THE INVENTION

This invention relates to reduced calorie fat substitutes which exhibit improved oxidative stability and flavor stability. More specifically, the invention pertains to esterified alkoxylated polyols as fat substitutes particularly a fatty acid-esterified propoxylated glycerol composition (EPG), wherein antioxidants have been added to the polyols and/or the fatty acids prior to their use in synthesis of fat substitutes, resulting in fat substitutes with superior stability.

RELATED ART

The quality of fats and oils deteriorates with time as a result of hydrolysis or oxidation. To reduce the potential for deterioration, steps are taken throughout oil recovery and processing to eliminate or minimize factors which catalyze hydrolysis or oxidation. These steps include the elimination or reduction of harmful microorganisms, the preservation of natural antioxidants in oils, the removal of heavy metals, pigments and other pro-oxidants and the exclusion of oxygen during processing and water during storage. The same or similar deterioration issues must also be addressed when producing fat or oil based fat substitutes.

Naturally occurring fats and oils contain characteristic antioxidants. In vegetable oils, these substances appear to protect the oil from degradation or deterioration during the normal life of the parent seed or fruit. The greater stability of vegetable oils to oxidative deterioration, as compared to animal fats, is generally attributable to their higher content of antioxidants. Unfortunately, antioxidants are, at least partially, removed from natural fats and oils during processing; particularly during steam stripping and deodorization. Commercially available natural and synthetic antioxidants can be added to finished oils to further protect them against oxidative degradation. Examples of commercially available antioxidants are "natural" tocopherols, propyl gallate, butylated hydroxyanisole (BHA), butylated hydroxytoluene (BHT) and tert-butylhydroquinone (TBHQ).

Although naturally occurring fats and oils contain characteristic antioxidants which combat deterioration, particularly oxidation, many attempts have been made to enhance the natural antioxidants and to make fats, oils and fat substitutes more resistant to oxidation.

In U.S. Pat. No. 4,973,681, a process is disclosed and claimed for increasing the stability of a polyol fatty acid polyester, particularly with respect to oxidation. The process requires contacting a polyol fatty acid polyester esterified to an extent of at least 40% with a polybasic oxy acid and separating the polyol fatty acid polyester from the polybasic oxy acid to obtain a polyol fatty acid polyester stabilized against oxidation.

A similar process is disclosed in Japanese Patent No. Sho-47-87709 (A), wherein a fat or oil is treated with a polybasic oxy acid to remove a trace amount of metal catalyst which had been employed during hydrogenation. The treatment is carried out for the purpose of restraining oxidation when the fat or oil is exposed to air.

In U.S. Pat. No. 5,064,677, edible fat containing products are disclosed which contain at least 5% of hardstock indigestible polyol fatty acid polyesters. These products are characterized by an improved combination of properties, particularly with regard to thermal stability and storage temperature cycle stability.

The present invention relates to a process which increases the stability of esterified alkoxylated polyols, particularly fatty acid-esterified propoxylated glycerol, through the addition of antioxidants to the components prior to the synthesis thereof. It has been surprisingly found that the addition of antioxidants during the synthesis of fat substitutes comprising fatty acid-esterified propoxylated glycerols produces final products with improved oxidative and flavor stability. It is believed that addition of the antioxidants during the earlier stages of synthesis allows their protective effects to be exhibited earlier by safeguarding the oils against degradation during their actual production.

SUMMARY OF THE INVENTION

Figure 1:
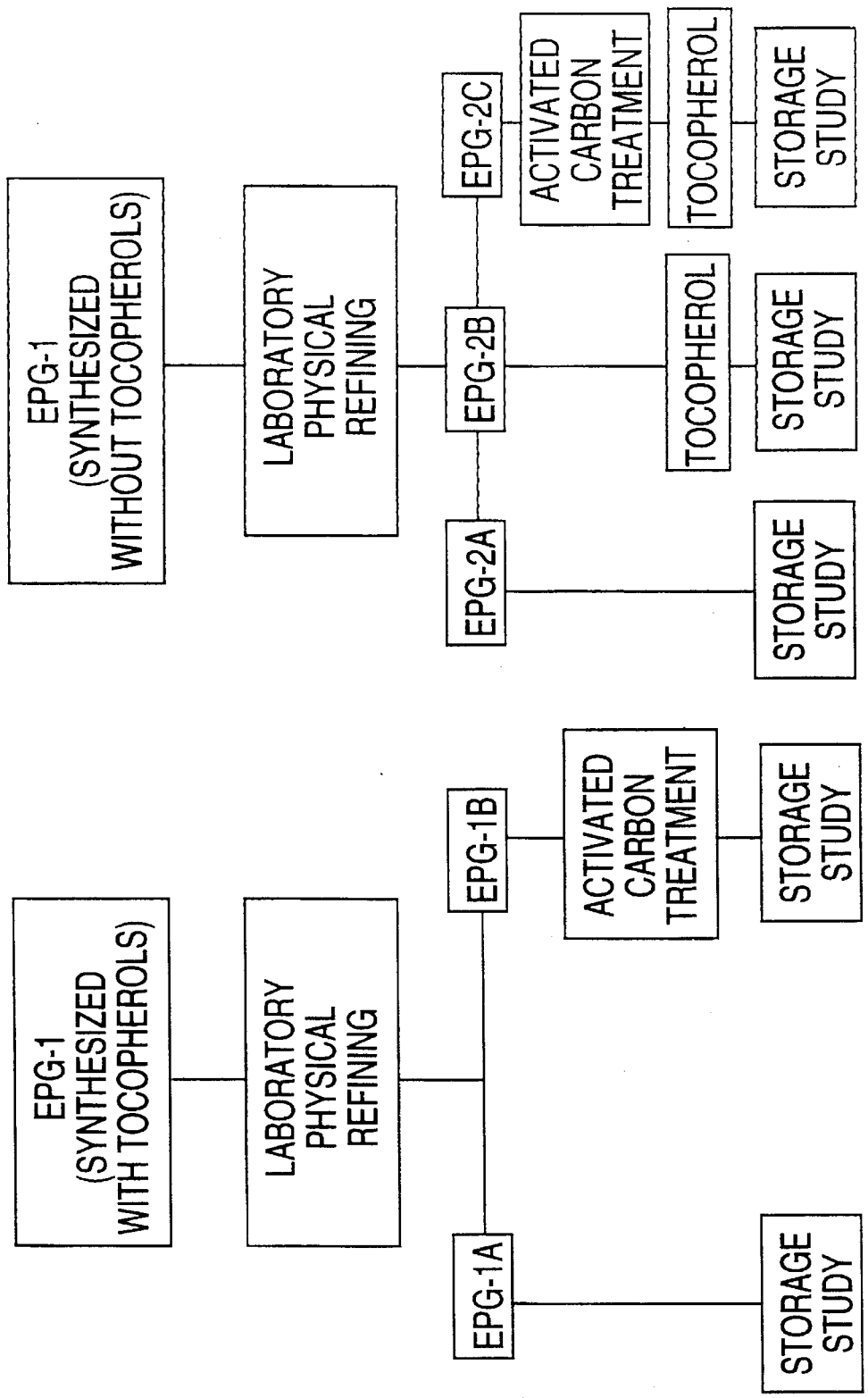
FIG. 1 is a flow chart showing the experimental design followed in Examples 1 and 2.
Figure 2:
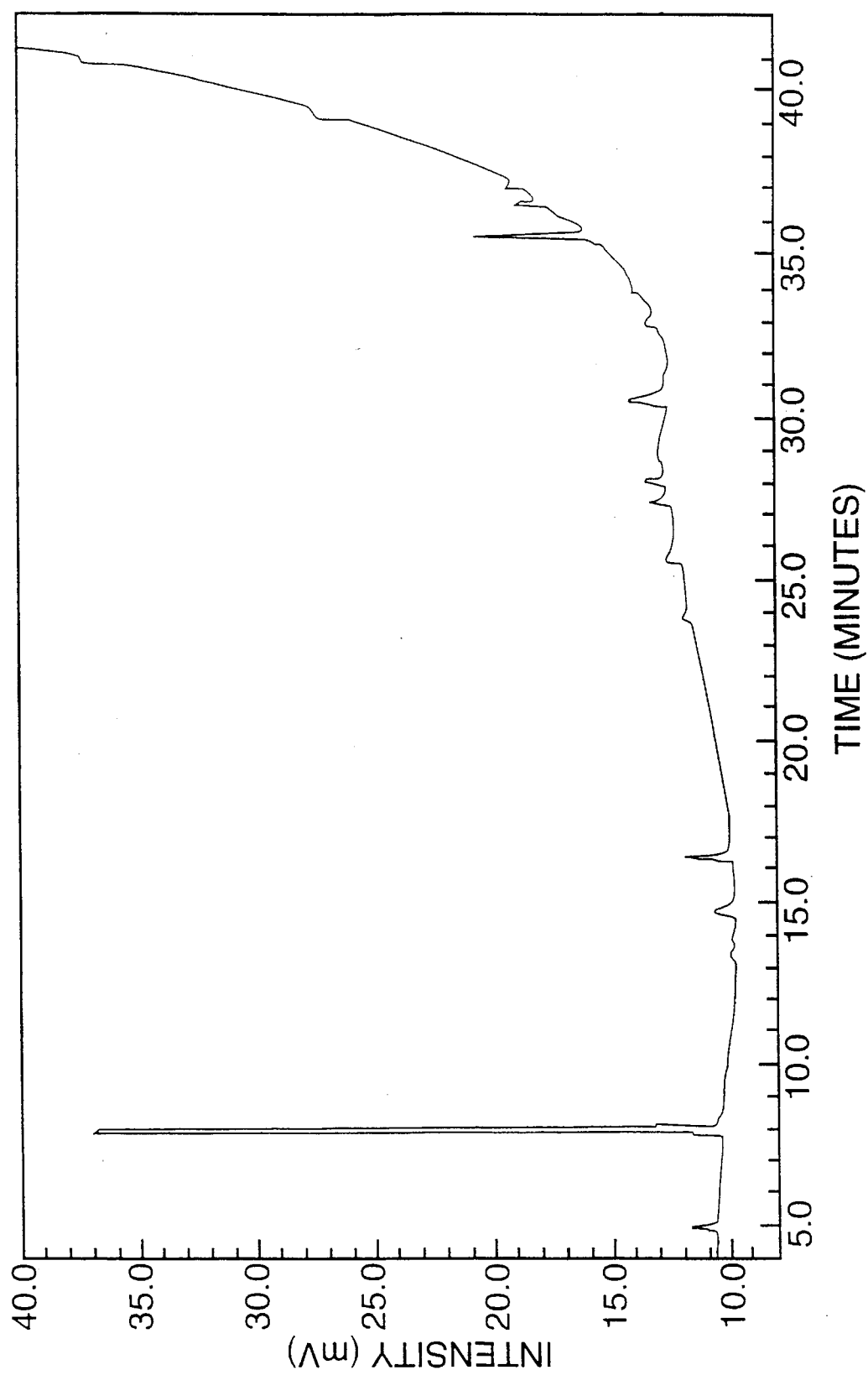
FIG. 2 is the chromatograph of the results of a headspace GC relative to Example 3.

Disclosed and claimed in U.S. Pat. No. 4,861,613 to Arco Chemical Technology, Inc., are esterified alkoxylated polyols, particularly esterified propoxylated glycerol (EPG), as non-digestible non-caloric fat substitutes which exhibit good organoleptic characteristics. However, these esterified alkoxylated polyols are similar to naturally occurring fats and oils in that they are sensitive to various physical elements, such as heat and light. When exposed to heat and light these polyols, including EPG, may experience both physical and chemical changes, such as oxidation, which result in odors, off color, and off flavors.

The present invention relates to fat substitutes, such as esterified alkoxylated polyols, particularly EPG, which exhibit improved oxidative and flavor stability. In particular, it has been found that the oxidative and flavor stabilities of esterified propoxylated glycerol are improved through the addition of antioxidants during glycerol alkoxylation and/or alkoxylated polyol esterification. It has been found that the esterified alkoxylated polyols, particularly EPG, synthesized in the presence of antioxidants yield a higher quality finished oil upon completion of the full processing sequence than an oil produced in the absence of antioxidants but having equivalent levels of antioxidants added following processing. This is contrary to traditional processing methods wherein antioxidants are added to oils or fats after processing has been completed but before the fats and oils are stored.

DETAILED DESCRIPTION

The present invention provides for the synthesis of esterified alkoxylated polyols in the presence of antioxidants to produce a finished product of higher quality which exhibits improved flavor and/or oxidative stability. Specifically, in the case of EPG, it has been found that the addition of antioxidants to its components prior to or during synthesis results in a product which has improved oxidative stability and flavor stability. The antioxidants can be added to the propoxylated polyols, the fatty acids or to both prior to their use in the synthesis process. This is contrary to the processes used for production of so-called "natural" oils and fats, and other fat substitutes wherein antioxidants are added to the fats and oils after processing has been completed.

Set forth in U.S. Pat. No. 4,983,329, and incorporated herein by reference, is the teaching of the preparation of esterified propoxylated glycerol (EPG) by reacting propoxylated glycerol having from 2 to 100 oxypropylene oxide units per glycerin and having a molecular weight of from about 200 to about 5900, with an excess of a saturated or unsaturated C10 to C24 fatty acid or mixtures thereof, at temperatures of from about 100° C. to about 250° C. Illustrative of such C10 to C24 fatty acids which may be employed include, for example, the saturated acids, such as capric, lauric, myristic, pentadecanoic, palmitic, heptadecanoic, stearic, nonadecanoic, n-eicosanoic, n-docosanoic and n-tetracosanoic. Unsaturated acids which may be employed include dodecylenic, palmitoleic, oleic, linoleic, linolenic, eicosenoic, arachidonic, docosahexaenoic and selacholeic. The fatty acids may be naturally occuring or synthetically produced. Similarly, mixtures of fatty acids may be used including those mixtures obtained by splitting natural or modified triglycerides, such as babassu oil, canola oil, cocoa butter, coconut oil, corn oil, cottonseed oil, jojoba oil, lard, meadowfoam oil, menhaden oil, olive oil, palm oil, palm kernel oil, peanut oil, rapeseed oil, rice bran oil, safflower oil, sesame seed oil, soybean oil, sunflower oil and tallow, or fully or partially hydrogenated mixtures thereof. Soya fatty acids which contain predominantly palmitic (9.8%), stearic (2.4%), oleic (28.9%), linoleic (50.7%) and linolenic (6.5%) along with minor amounts of lauric, myristic, arachidic, palmitoleic and behenic acid may also be employed in the present invention.

The reactive steps in the production of EPG, i.e. propoxylation of the glycerol, and esterification of the propoxylated glycerol with an excess of saturated or unsaturated fatty acids, may be carried out in any suitable reactor which is generally equipped with a means for agitation and a means for regulating temperature and pressure. The reaction may be carried out as a batch or a continuous process.

In accordance with the present invention, the antioxidants are added to the individual components of EPG, instead of to the finished product. Therefore, the antioxidants can be added to either the polyols, such as propoxylated glycerol, or the fatty acid, or both, prior to reacting. The antioxidants should be added at total levels up to about 1.0% by weight, preferably from about 0.05 to about 0.2% by weight.

The antioxidants can be added to the polyols at various stages throughout the process. The first stage at which the antioxidant can be added is to the crude propoxylated glycerol prior to catalyst removal or steam stripping. Catalyst removal can be accomplished via magnesol treatment, acid addition, ion exchange or other suitable processes known in the art. Steam stripping is used to remove light by-products from the propoxylated glycerol. By adding the antioxidants to the propoxylated polyol, the formation of light by-products is greatly reduced, thereby reducing the amount of steam stripping required. Despite the fact that much of the antioxidant is removed during steam stripping, the resultant product exhibits increased stability against oxidation and off-flavors.

An alternate embodiment provides for the addition of the antioxidants to the propoxylated polyol subsequent to steam stripping but prior to esterification with fatty acids. This procedure will also result in a final product which exhibits increased stability. A third alternative is a process whereby the antioxidants are directly added to the fatty acids prior to esterification, instead of being added to the propoxylated polyol. This method also results in an esterified propoxylated polyol which exhibits the desired improvements in flavor stability and oxidative stability. Alternately, antioxidants can be added to combinations of both the fatty acids and the propoxylated polyols, whether crude or stripped, which will also result in esterified propoxylated polyols which exhibit the desired beneficial results. It should be noted, however, that the point of addition of the antioxidants has no effect on the processing of the esterified alkoxylated polyol, such as fatty acid-esterified, propoxylated glycerol, and despite some losses of antioxidant during processing, products which exhibit higher levels of stability than those resulting from standard processing ultimately result.

The preferred antioxidants are so-called "natural" antioxidants, but synthetic antioxidants, such as butylated hydroxytoluene (BHT), butylated hydroxyanisole (BHA), tertiary-butylhydroquinone (TBHQ) or propyl gallates, may also be employed. Natural antioxidants include tocopherols, various cereal and seed extracts, such as extracts from sesame and oats, phospholipids, organic acids, and proteins. However, the most widely known and most likely used in crude or refined vegetable oils are tocopherols. The tocopherols most commonly used are actually mixtures of four tocopherols; $\alpha$; $\beta$; $\gamma$ and $\delta$. It has been customary in recent years to supplement natural antioxidants with the synthetic antioxidants, reducing or chelating agents, such as L-ascorbyl palmitate, erythorbic acid, citric acid or EDTA, with some indications of synergistic effects from the combination. In the present invention, it is acceptable to use either the natural antioxidants, particularly tocopherols, alone or in combination with synthetic antioxidants or the reducing or chelating agents. It is, of course, also acceptable to use synthetic antioxidants alone, i.e. not combined with any natural antioxidants.

The inclusion of the antioxidants during synthesis results in a lower peroxide value (PV), which is a measure of the amount of peroxides present expressed as milli-equivalents of peroxide-oxygen per kilogram of fat. Peroxides, particularly, hydroperoxides, are relatively unstable compounds which act as precursors for the formation of a wide variety of degraded compounds, which are responsible for off-flavor. By "mopping up" free peroxide radicals, antioxidants, such as tocopherols, interrupt the free radical chain of oxidative reactions and assist greatly in the delay of the development of off-flavors.

The addition of antioxidants during synthesis also results in a lower anisidine value (AV). This test determines the level of secondary oxidation products, primarily aldehydes (such as 2-alkenals and 2,4-dienals) that are present in an oil. The anisidine value is defined as one hundred (100) times the absorbance of a solution resulting from the reaction of 1 gram of oil or fat in 100 ml of a mixture of solvent and p-anisidine, measured in a 1 cm cell at 350 mm under the conditions of the test. This value is often used in conjunction with the PV to calculate a total oxidation value, or oxi-index (PV/3+AV). The anisidine test has been adopted by many within the oil industry as a standard method for determination of secondary oxidation products in an oil.

Another surprising result of the addition of the antioxidants prior to or during synthesis of esterified alkoxylated polyols, particularly fatty acid-esterified propoxylated glycerol, is that the improved flavor stability and oxidative stability is apparent despite the loss of antioxidant during synthesis and processing. Analysis indicates that less than 10% of the original amount of antioxidants, added prior to fatty acid esterification remain in the finished product, particularly in the case of tocopherols. Additional analysis shows minimal presence of tocopherol esters. Thus, it is believed that the majority of the tocopherols added as antioxidants are stripped from the oil during its synthesis and subsequent processing. It is also found that the addition of antioxidants after processing does not result in a product which exhibits the same peroxide or anisidine values.

The following examples are meant to be illustrative and are not meant to be a limitation of the invention, the metes and bounds of which are set forth in the claims.

EXAMPLE 1

One batch of esterified propoxylated glycerol (EPG-1) was synthesized in accordance with the process disclosed in U.S. Pat. No. 4,983,329 hereby incorporated by reference. EPG-1 was synthesized in the presence of 1200 ppm of mixed tocopherols (0.24% TENOX GT-1, Eastman Chemical Products, Kingsport, Tenn.). The tocopherols were added to the stripped propoxylated glycerol prior to fatty acid esterification. The mixture was heated to 240° C. (465° F.) and a nitrogen purge was carried out at the minimum rate necessary to remove the water.

the presence of added tocopherols. After physical refining in the laboratory, EPG-2 was divided into 3 samples; EPG-2A, EPG-2B and EPG-2C. EPG-2C was subjected to activated carbon treatment subsequent to physical refining as set forth in Example 1. Additionally, tocopherols (TENOX GT-1) were added to samples EPG-2B and EPG-2C subsequent to processing but prior to storage (See FIG. 1). The Tenox GT-1 was added at 0.24% by weight yielding a final tocopherol level which is typical for vegetable oils and equivalent to that used in Example 1. The resulting oils were stored and evaluated as described in Example 1.

Table 1 sets forth the results obtained in Examples 1 and 2. Examination of these results clearly shows that the superior results were obtained with sample EPG-1A wherein the EPG was synthesized with tocopherols prior to processing, and not subjected to activated carbon treatment. This conclusion is based on the resultant PV and corresponding Oxi-Index. Additionally, its flavor, as evidenced by both the strength and descriptor measurements, was the most desirable of the samples.

TABLE 1

| Sample | Sample Time: (wk) | Color, red 5.25" cell | PV | AV | Oxi-Index (⅓ PV + AV) | Flavor Strength | Descriptors |
|---|---|---|---|---|---|---|---|
| EPG-1A | 0 | 0.4 | 0.2 | 2.5 | 2.6 | | |
| | 4 | 0.4 | 2.9 | 2.7 | 3.7 | 3.5 | nutty & painty |
| | 6 | 0.4 | 6.4 | 3.1 | 5.2 | 3.5 | nutty & painty |
| | 12 | 0.4 | 4.8 | 3.2 | 4.8 | 2.7 | buttery |
| | 15 | 0.4 | 8.6 | 3.4 | 6.2 | | |
| EPG-1B | 0 | 0.4 | 0.2 | 2.4 | 2.5 | | |
| | 4 | 0.3 | 3.2 | 2.2 | 3.3 | 4.0 | nutty & painty |
| | 6 | 0.3 | 3.7 | 2.9 | 4.1 | 4.0 | nutty & painty |
| | 12 | 0.3 | 11.4 | 3.0 | 6.8 | 3.0 | hydro |
| | 15 | 0.3 | 11.1 | 3.5 | 7.2 | | |
| EPG-2A | 0 | 0.5 | 0.7 | 3.3 | 3.5 | | |
| | 4 | 0.5 | 2.3 | 2.7 | 3.5 | 5.5 | painty |
| | 6 | 0.5 | 5.5 | 3.9 | 5.7 | 5.5 | painty |
| | 12 | 0.5 | 12.3 | 4.1 | 8.2 | 5.5 | painty |
| | 15 | 0.4 | 11.4 | 4.3 | 8.1 | | |
| EPG-2B | 0 | 0.5 | 0.6 | 3.6 | 3.8 | | |
| | 4 | 0.5 | 1.9 | 3.1 | 3.7 | 5.0 | painty |
| | 6 | 0.5 | 5.3 | 4.1 | 5.8 | 5.0 | painty |
| | 12 | 0.4 | 13.7 | 4.4 | 8.9 | 3.5 | hydro/fruity |
| | 15 | 0.4 | 11.9 | 4.6 | 8.5 | | |
| EPG-2C | 0 | 0.4 | 1.2 | 3.1 | 3.5 | | |
| | 4 | 0.4 | 3.2 | 2.9 | 4.0 | 5.0 | painty |
| | 6 | 0.4 | 4.0 | 6.0 | 7.3 | 5.0 | painty |
| | 12 | 0.3 | 10.7 | 6.5 | 10.0 | 4.0 | |
| | 15 | 0.3 | 10.3 | 6.6 | 10.0 | | |

EPG-1 was then physically refined in the laboratory. EPG-1 was divided into two samples; EPG-1A and EPG-1B. EPG-1B was subjected to activated carbon treatment subsequent to physical refining. The treatment consisted of mixing 0.1% DARCO KB (American Norit Co. Inc., Jacksonville, Fla.) activated carbon in the oil followed by filtration through a bed of filteraid. FIG. 1 clearly sets forth the experimental design for Examples 1 and 2 contained in this application. The oils were stored in 8 oz. glass bottles, loosely capped at ambient temperatures under indoor fluorescent lights. Samples were withdrawn periodically and evaluated for flavor, color and oxi-index. The results are set forth in Table 1.

EXAMPLE 2

One batch of EPG (EPG-2) was synthesized as set forth in Example 1, except that EPG-2 was synthesized without

EXAMPLE 3

503 pounds of glycerin were propoxylated with 1,564 pounds of propylene oxide. The resulting propoxylated glycerol was treated with 60 pounds of Magnesol (Reagent Chemcial & Research Inc., Jeffersonville, Ind.) mixed with Celite (521, Aldrich #22,179-1, Milwaukee, Wis.) at a temperature of 93° C. (200° F.) for a period of one hour. The product resulting from this treatment was filtered and the resulting product was subjected to a second treatment with 60 pounds of magnesol and 6 pounds of Celite. The product was filtered after the second treatment, and, 21.9 grams of TBHQ were added to the treated polyol which was then subjected to steam stripping at 149° C. (300° F.) at maximum vacuum (approximately 20 mm Hg) for a period of one hour. After stripping, an additional 43.8 grams of TBHQ were added to the polyol prior to esterification. Headspace GC was conducted on the stripped polyol and the results as shown in FIG. 2, demonstrated the minimal amount of light byproducts produced during the processing.

EXAMPLE 4

Figure 3:
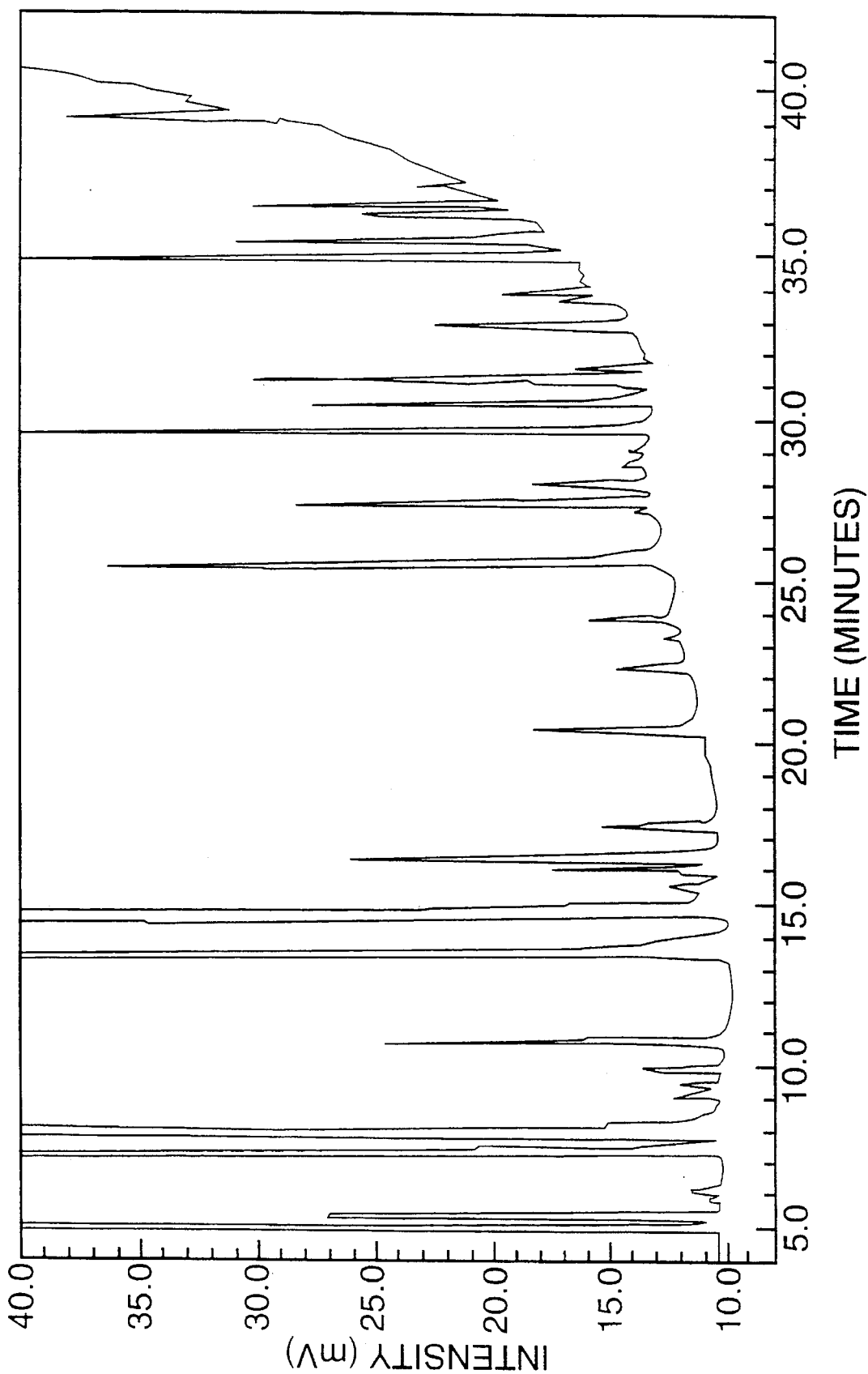
FIG. 3 is the chromatograph of the results of a headspace GC relative to Example 4.

501 pounds of glycerin were propoxylated with 1,558 pounds of propylene oxide. The resulting propoxylated glycerol was treated with 60 pounds of Magnesol mixed with Celite (521, Aldrich #22,179-1, Milwaukee, Wis.) at a temperature of 93° C. (200° F.) for a period of one hour. The product resulting from this treatment was filtered and the resulting product was subjected to a second treatment with 60 pounds of magnesol and 6 pounds of celite. The treated polyol was then steam stripped for one hour at 149° C. (300° F.) at approximately 20 mm Hg vacuum. After stripping, headspace GC was conducted and the results, as shown in FIG. 3, indicated the presence of a large number of light byproducts.

We claim:

1. A method for the preparation of an esterified alkoxylated polyol exhibiting improved oxidative and flavor stability which comprises the steps of:
   (a) alkoxylating the polyol;
   (b) esterifying the alkoxylated polyol with an excess of saturated or unsaturated fatty acids; and
   (c) steam stripping the esterified alkoxylated polyol;
   wherein an antioxidant is added to the alkoxylated polyol or the fatty acids.

2. The method of claim 1 wherein the antioxidant is added to the alkoxylated polyol resulting from step a).

3. The method of claim 1 wherein the antioxidant is added to the fatty acids prior to esterification in step b).

4. The method of claim 1, wherein the antioxidant is separately added to the alkoxylated polyol and to the fatty acids prior to esterification in step b).

5. The method of claim 1 wherein the antioxidant is chosen from the group consisting of natural antioxidants, synthetic antioxidants and combinations thereof.

6. The method of claim 1 wherein the antioxidant is mixed tocopherols.

7. The method of claim 1 wherein the antioxidant is chosen from the group consisting of butylated hydroxytoluene, butylated hydroxyanisole, tertiary-butylhydroquinone, propyl gallates and combinations thereof.

8. The method of claim 1 which further comprises steam stripping of the alkoxylated polyol prior to esterification.

9. The method of claim 8 wherein the antioxidant is added to the alkoxylated polyol after steam stripping and prior to esterification.

10. The product of claim 1.

11. A method for the preparation of an esterified propoxylated glycerol which comprises the steps of:
    (a) propoxylating glycerol; and
    (b) esterifying the propoxylated glycerol with an excess of saturated or unsaturated fatty acids; and
    (c) steam stripping—the esterified propoxylated glycerol, wherein an antioxidant is added to the propoxylated glycerol or the fatty acids.

12. The method of claim 11 wherein the antioxidant is added to the propoxylated glycerol resulting from step a).

13. The method of claim 11 wherein the antioxidant is added to the fatty acids prior to esterification in step b).

14. The method of claim 11, wherein the antioxidant is separately added to the propoxylated glycerol and to the fatty acids prior to esterification in step b).

15. The method of claim 11, wherein the antioxidant is chosen from the group consisting of natural antioxidants, synthetic antioxidants and combinations thereof.

16. The method of claim 11 wherein the antioxidants is mixed tocopherols.

17. The method of claim 11 wherein the antioxidant is chosen from the group consisting of butylated hydroxytoluene, butylated hydroxyanisole, tertiary-butylhydroquinone, propyl gallates and combinations thereof.

18. The method of claim 11 which further comprises steam stripping the propoxylated glycerol prior to esterification.

19. The method of claim 18 wherein the antioxidant is added to the propoxylated glycerol after the steam stripping and prior to esterification.

20. The product of claim 11.

21. An esterified propoxylated glycerol which exhibits improved flavor and oxidative stability and which comprises the addition of antioxidants to the glycerol, fatty acids, or combinations thereof, during processing.

* * * * *

UNITED STATES PATENT AND TRADEMARK OFFICE
CERTIFICATE OF CORRECTION

PATENT NO. : 5,571,935
DATED : November 5, 1996
INVENTOR(S) : Bernard C. Sekula, et al.

It is certified that error appears in the above-identified patent and that said Letters Patent is hereby corrected as shown below:

Claim 1, column 7, line 28, after "acids" add -- prior to esterification and does not bond to the polyol during esterification --
(See Statement of Reasons for Allowance mailed June 11, 1996 with the Notice of Allowance.)

Claim 11, column 8, line 15, after "acids" add -- prior to esterification and does not bond to the polyol during esterification --
(See Statement of Reasons for Allowance mailed June 11, 1996 with the Notice of Allowance.)

Claim 16, column 8, line 26, delete "antioxidants" and substitute therefor -- antioxidant --
(See Amendment filed August 31, 1995.)

Signed and Sealed this

Twenty-seventh Day of May, 1997

Attest:

BRUCE LEHMAN

*Attesting Officer*       Commissioner of Patents and Trademarks

UNITED STATES PATENT AND TRADEMARK OFFICE
CERTIFICATE OF CORRECTION

PATENT NO. : 5,571,935
DATED : November 5, 1996
INVENTOR(S) : Bernard C. Sekula, et al.

It is certified that error appears in the above-identified patent and that said Letters Patent are hereby corrected as shown below:

On the title page, item [73]
Assignee column, after "N.J." add -- and ARCO Chemical Technology, L.P., Greenville, DE. --

Signed and Sealed this

Second Day of June, 1998

Attest:

BRUCE LEHMAN

Attesting Officer    Commissioner of Patents and Trademarks